US009849214B2

(12) United States Patent
Woodell-May et al.

(10) Patent No.: US 9,849,214 B2
(45) Date of Patent: Dec. 26, 2017

(54) POROUS ORTHOPEDIC MATERIALS COATED WITH DEMINERALIZED BONE MATRIX

(71) Applicant: Biomet Manufacturing, LLC, Warsaw, IN (US)

(72) Inventors: Jennifer Woodell-May, Warsaw, IN (US); Karen Troxel, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 49 days.

(21) Appl. No.: 14/636,487

(22) Filed: Mar. 3, 2015

(65) Prior Publication Data
US 2015/0174295 A1 Jun. 25, 2015

Related U.S. Application Data

(63) Continuation of application No. 11/688,912, filed on Mar. 21, 2007, now abandoned.

(51) Int. Cl.
| A61K 8/98 | (2006.01) |
|---|---|
| A61L 27/36 | (2006.01) |
| A61L 31/00 | (2006.01) |
| A61L 31/10 | (2006.01) |
| A61L 31/12 | (2006.01) |
| A61L 31/14 | (2006.01) |
| A61L 27/04 | (2006.01) |
| A61L 27/06 | (2006.01) |
| A61L 27/12 | (2006.01) |
| A61L 27/54 | (2006.01) |
| A61L 27/56 | (2006.01) |
| A61L 27/58 | (2006.01) |

(52) U.S. Cl.
CPC ......... *A61L 27/3608* (2013.01); *A61L 27/042* (2013.01); *A61L 27/045* (2013.01); *A61L 27/047* (2013.01); *A61L 27/06* (2013.01); *A61L 27/12* (2013.01); *A61L 27/54* (2013.01); *A61L 27/56* (2013.01); *A61L 27/58* (2013.01); *A61L 31/005* (2013.01); *A61L 31/10* (2013.01); *A61L 31/124* (2013.01); *A61L 31/146* (2013.01); *A61L 2300/30* (2013.01); *A61L 2300/414* (2013.01); *A61L 2300/606* (2013.01); *A61L 2420/02* (2013.01); *A61L 2420/06* (2013.01); *A61L 2430/02* (2013.01)

(58) Field of Classification Search
CPC .............................. A61K 8/0279; A61K 8/98
See application file for complete search history.

(56) References Cited

U.S. PATENT DOCUMENTS

| 4,294,753 A | 10/1981 | Urist |
|---|---|---|
| 4,976,736 A | 12/1990 | White et al. |
| 5,073,373 A | 12/1991 | O'Leary et al. |
| 5,284,655 A | 2/1994 | Bogdansky et al. |
| 5,290,558 A | 3/1994 | O'Leary et al. |
| 6,118,043 A | 9/2000 | Nies et al. |
| 6,206,924 B1 | 3/2001 | Timm |
| 6,261,586 B1 | 7/2001 | McKay |
| 6,376,573 B1 | 4/2002 | White et al. |
| 6,451,059 B1 | 9/2002 | Janas et al. |
| 6,527,810 B2 | 3/2003 | Johnson et al. |
| 6,551,995 B1 | 4/2003 | Oppermann et al. |
| 6,565,884 B2 | 5/2003 | Nimni |
| 6,576,089 B1 | 6/2003 | Sato et al. |
| 6,576,249 B1 | 6/2003 | Gendler et al. |
| 6,613,089 B1 | 9/2003 | Estes et al. |
| 6,692,790 B2 | 2/2004 | Liu et al. |
| 6,989,033 B1 | 1/2006 | Schmidt |
| 2002/0192263 A1* | 12/2002 | Merboth .................. A61K 6/08 424/426 |
| 2003/0009235 A1 | 1/2003 | Manrique et al. |
| 2003/0044445 A1 | 3/2003 | Kay et al. |
| 2004/0265385 A1 | 12/2004 | West et al. |
| 2005/0142164 A1 | 6/2005 | Lindholm et al. |
| 2005/0175657 A1 | 8/2005 | Hunter et al. |
| 2005/0201987 A1 | 9/2005 | Pirhonen et al. |
| 2006/0241776 A1 | 10/2006 | Brown et al. |
| 2006/0241781 A1 | 10/2006 | Brown et al. |
| 2006/0271201 A1 | 11/2006 | Kumar et al. |

OTHER PUBLICATIONS

"U.S. Appl. No. 11/688,912, Final Office Action dated Jun. 25, 2010", 7 pgs.
"U.S. Appl. No. 11/688,912, Final Office Action dated Sep. 23, 2014", 9 pgs.
"U.S. Appl. No. 11/688,912, Non Final Office Action dated May 5, 2014", 6 pgs.
"U.S. Appl. No. 11/688,912, Non Final Office Action dated Dec. 29, 2009", 7 pgs.
"U.S. Appl. No. 11/688,912, Notice of Non-Compliant Amendment dated Oct. 28, 2010", 2 pgs.
"U.S. Appl. No. 11/688,912, Response filed Mar. 29, 2010 to Non Final Office Action dated Dec. 29, 2009", 10 pgs.
"U.S. Appl. No. 11/688,912, Response filed Jul. 28, 2014 to Non Final Office Action dated May 5, 2014", 11 pgs.
"U.S. Appl. No. 11/688,912, Response filed Oct. 8, 2009 to Restriction Requirement dated Sep. 8, 2009", 11 pgs.

(Continued)

*Primary Examiner* — Ruth Davis

(74) *Attorney, Agent, or Firm* — Schwegman Lundberg & Woessner, P.A.

(57) ABSTRACT

A biomaterial including a porous biocompatible structure having interconnected pores, wherein the pores have interior walls and are interconnected by passageways, the interior walls and passageways being coated with an osteoinductive aqueous demineralized bone extract solution, the aqueous demineralized bone extract solution including growth factors, proteins, a demineralized bone matrix and at least one of a weak acid and a guanidine hydrochloride, wherein the demineralized bone matrix is present per 100 g of the solution in an amount of from about 2 g to about 10 g.

20 Claims, No Drawings

(56) References Cited

OTHER PUBLICATIONS

"U.S. Appl. No. 11/688,912, Response filed Oct. 22, 2010 to Final Office Action dated Jun. 25, 2010", 15 pgs.
"U.S. Appl. No. 11/688,912, Response filed Nov. 4, 2010 to Notice of Non-Compliant Amendment dated Oct. 28, 2010", 9 pgs.
"U.S. Appl. No. 11/688,912, Restriction Requirement dated Sep. 8, 2009", 6 pgs.
"U.S. Appl. No. 11/688,912, Supplemental Amendment filed Oct. 13, 2009", 11 pgs.
"International Application Serial No. PCT/US2008/057707, International Search Report dated Oct. 5, 2009", 3 pgs.
"International Application Serial No. PCT/US2008/057707, Written Opinion dated Oct. 5, 2009", 6 pgs.
Han, Bo, et al., "Quantitative and Sensitive In Vitro Assay for Osteoinductive Activity of Demineralized Bone Matrix, Journal of Orthopaedic Research", Journal of Orthopaedic Research, vol. 21, (2003), 648-654.
Wei-Qi, Yan, et al., "Bone Bonding in Bioactive Glass Ceramic Combined with Bone Matrix Gelatin", Journal of Biomedical Materials Research, vol. 42, No. 2, (1998), 258-265.
Xudong, Li, et al., "Demineralized Bone Matrix Gelatin as Scaffold for Osteochondral Tissue Engineering", Biomaterials vol. 27, No. 11, (2006), 2426-2435.

\* cited by examiner

POROUS ORTHOPEDIC MATERIALS COATED WITH DEMINERALIZED BONE MATRIX

CROSS-REFERENCE TO RELATED APPLICATIONS

This application is a continuation of U.S. patent application Ser. No. 11/688,912 filed Mar. 21, 2007, and entitled "Porous Orthopedic Materials Coated with Demineralized Bone Matrix," the disclosure of which is expressly incorporated in its entirety herein by this reference.

TECHNICAL FIELD

This invention relates generally to coated porous orthopedic materials and more specifically to porous orthopedic materials coated with demineralized bone matrix extracts comprising growth factors.

BACKGROUND OF THE INVENTION

Prosthetic devices and bone implants can either be made of resorbable or non-resorbable materials. In particular, current bone graft materials include autografts (bone material obtained from the patient), allografts (cadaver bone and bone material typically obtained from tissue banks); xenografts (bone materials from animals), and a variety of artificial or synthetic bone substitute materials. Such bone substitute materials include materials that are biocompatible with existing bone, tendon, cartilage and ligaments, and may comprise metals, ceramics, or composite materials. Although synthetic materials can be designed to have porous structures that can accommodate de-novo bone in-growth, they are generally considered inadequate as being non-osteoinductive.

The prior art has extracted growth factors from demineralized bone matrix (DBM) to be used as a surface coating or a putty to induce bone growth into implant materials. Demineralized bone matrix (DBM) is a well characterized osteoinductive resorbable material containing growth factors, osteogenic proteins and collagen, which has also been extracted from DBM to be used as a gel coating for implant materials. U.S. Patent Application No. 2003/0044445 discloses a DBM soluble extract of proteins that is dried, reconstituted and then mixed with demineralized bone particles to provide a bone filling material. However, there is no teaching of applying a DBM soluble extract to a porous synthetic implant material where the extract coats within the pores.

Alternatively, U.S. Pat. No. 6,576,249 discloses a method for preparing a bone gel and bone putty by dissolving DBM in water, allowing it to form a gel and mixing it with non-demineralized bone particles to form putty. The '249 patent does not disclose using this material as a coating. The presence of the bone particles in the material would prohibit it from coating the pores of a porous implant material.

U.S. Pat. No. 6,376,573 discloses a porous ceramic implant material of coralline hydroxyapatite having a coating within the pores of the material. The coating however, is used to reinforce the implant material and not to promote bone growth. The coating therefore cannot fill the pores, but must only be on the walls of the pores. This is accomplished by adding the coating as a liquid and then catalyzing the conversion to a polymeric material in situ.

As can be seen, there is a need for a coating material for porous implants that promotes bone growth, allowing the integration of the implant within the patient. It would be desirable for the coating to comprise growth factors, including osteoinductive proteins to promote the bone growth.

SUMMARY OF THE INVENTION

In one aspect of the present invention there is provided a biomaterial comprising a porous biocompatible structure comprising interconnected pores, wherein the pores comprise interior walls and may be interconnected by passageways, an aqueous demineralized bone extract coating comprising growth factors, proteins or a combination thereof, a demineralized bone gelatin coating comprising a demineralized bone matrix gelatin, and wherein the demineralized bone extract coating and the demineralized bone gelatin coating may cover the interior walls and passageways. The demineralized bone extract coating and the demineralized bone gelatin coating may be combined into a single coating before being applied to the porous biocompatible substrate. Alternatively, the demineralized bone extract coating may be applied to the porous biocompatible substrate and then the demineralized bone gelatin coating may be applied over the demineralized bone extract coating.

In another aspect of the present invention, there is provided a biomaterial comprising a porous biocompatible structure comprising interconnected pores, wherein the pores comprise interior walls and are interconnected by passageways and an aqueous demineralized bone extract coating comprising growth factors, proteins or a combination thereof, wherein the demineralized bone extract coating covers the interior walls and passageways.

In a further aspect of the present invention, there is provided an orthopedic implant comprising a porous biocompatible structure comprising interconnected pores, wherein the pores comprise interior walls and are interconnected by passageways and wherein the pores have an average diameter of from about 200 microns to about 500 microns and an aqueous demineralized bone extract coating comprising growth factors, proteins or a combination thereof, wherein the demineralized bone extract coating covers the interior walls and passageways, wherein the bone extract coating is dried on the interior walls and passageways.

In yet another aspect of the present invention there is provided a method of preparing a biomaterial comprising mixing demineralized bone with an aqueous solution, the aqueous solution comprising a weak acid or guanidine hydrochloride, and wherein the mixing proceeds with constant agitation at a temperature of no greater than 50° C. for a time period of from about 8 hours to about 96 hours to prepare a demineralized bone extract; separating the demineralized bone extract from any remaining solids; diluting, removing or neutralizing the weak acid or guanidine hydrochloride in the demineralized bone extract; coating a porous biocompatible structure with the demineralized bone extract, wherein the porous biocompatible structure has a porosity comprising interconnected pores, the pores comprising interior walls and interconnected by passageways, and wherein the demineralized bone extract infiltrates the pores and coats the interior walls and passageways; and drying the applied demineralized bone extract onto the porous biocompatible structure. The method may further comprise the steps of mixing the solids separated from the extract with an aqueous saline solution to form a suspension; heating the suspension to a temperature of from about 85° C. to about 130° C. at a pressure of at least 15 psig, dissolving the demineralized bone to produce a demineralized bone gelatin; and mixing the demineralized bone gelatin with the demineralized bone extract before coating the biocompatible structure. Alternatively, the method may further comprise the steps of mixing the solids separated from the extract with an aqueous saline solution to form a suspension; heating the suspension to a temperature of from about 85° C. to about 130° C. at a pressure of at least 15 psig, dissolving the demineralized bone to produce a demineralized bone gelatin solution; applying the demineralized bone gelatin solution over the dried demineralized bone extract on the biocompatible structure, wherein the demineralized bone gelatin solution infiltrates the pores and coats the internal walls and passageways; allowing the applied demineralized bone gelatin solution to gel; and lyophilizing the biocompatible structure and the applied demineralized bone gelatin solution.

These and other features, aspects and advantages of the present invention will become better understood with reference to the following description and claims.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides a biomaterial comprising a porous biocompatible structure that may be coated with a demineralized bone (DBM) extract comprising growth factors that increase de novo bone growth into the porous composite material. Methods are also provided for making the biomaterial of the present invention. The biomaterial may further comprise a demineralized bone gelatin coating over the extract coating or the demineralized bone extract may be combined with the gelatin coating. The biomaterial is coated such that the pores and any connecting passageways are coated to support, but not block, bone growth into the biomaterial. The biomaterial may be in a form such as, but not limited to, granules, blocks, cylinders or pre-formed shapes such as hip or knee augments, hip or knee implants, or other orthopedic devices.

The biomaterial of the present invention may comprise a porous biocompatible structure where the porous biocompatible structure comprises pores interconnected by passageways. The porous biocompatible structure may be coated with an osteoinductive coating such that the coating is not only on the surface but may also coat the pores and passageways. It has been discovered that by coating the pores and the passageways, bone growth into the porous material may be scattered throughout most of the implant compared to the porous biomaterial alone or the porous biomaterial with just a gelatin coating. In contrast to the present invention, coatings of the prior art coat the outer surface of a biomaterial with a gelatin coating and are not designed to be used solely on a porous substrate. Many of the coatings of the prior art comprise demineralized bone powder which, although finely milled, prohibits the coating from completely coating the pores and passageways of a porous biomaterial and may even clog the pores. Other coatings of the prior art have been designed to strengthen porous biomaterials and are not osteoinductive.

In one embodiment, the biomaterial of the present invention may comprise a porous biocompatible structure which may comprise interconnected pores. The pores may comprise interior walls and may be connected by passageways. In one illustrative embodiment, the pores may have an average size from about 5 microns to 1000 microns or from about 200 microns to about 500 microns. In another illustrative embodiment, the porous biocompatible structure may be resorbable as new bone is formed or may be non-resorbable. The resorbable biocompatible structure may be, but not limited to, hydroxyapatite. The hydroxyapatite may be tricalcium phosphate such as, but not limited to, Calcigen® PSI. Alternatively, the hydroxyapatite may be a coralline hydroxyapatite such as, but not limited to, the coralline hydroxyapatite described in U.S. Pat. No. 4,976,736 (herein incorporated by reference), known under the trade name Pro Osteon™. By way of non-limiting example, the coralline hydroxyapatite may be Pro Osteon™ 200 or Pro Osteon™ 500 which may have an average pore size of 200 microns and 500 microns, respectively. In an alternate illustrative embodiment, the resorbable biocompatible structure may be, but not limited to, xenograft demineralized cancellous bone. The demineralized cancellous bone may be formed from cancellous bone from an animal such as, but not limited to, pig, cow or horse. The cancellous bone may be cleaned to remove all blood and marrow from the pores. The bone is then demineralized in hydrochloric acid or any other procedure known in the art. Following the demineralization, the bone may be washed and extracted guanidine hydrochloride. The remaining porous collagen structure that may have the architecture of cancellous bone may then be used in the present invention. In a further illustrative embodiment the porous biocompatible structure may be non-resorbable. By way of a non-limiting example, the non-resorbable biocompatible structure may comprise porous metal where the metal may be stainless steel, titanium, titanium alloy, tantalum or cobalt-chromium alloy. Examples of porous metal for use as implant material may be found in U.S. Pat. Nos. 6,206,924, 7,597,715 and 8,292,967, all of which are incorporated herein by reference. The porous biocompatible structure may have a form such as, but not limited to, granules, blocks, cylinders or pre-formed shapes such as hip or knee augments, hip or knee implants, or other orthopedic devices.

The biomaterial may further comprise an aqueous demineralized bone extract coating comprising growth factors, proteins or a combination thereof. It will be appreciated that many growth factors may be proteins and the two categories are not mutually exclusive, one is not a subset of the other. The growth factors or proteins may be osteoinductive, helping to promote de novo growth of new bone. Non-limiting examples of growth factors may be bone morphogenic proteins, particularly BMP-2 and BMP-7, TGF-β, IGF-1, VEGF, PDGF, FGF, EGF or mixtures thereof. The aqueous demineralized bone extract coating may also comprise biologic solutions such as, but not limited to, blood, platelet rich plasma, platelet poor plasma concentrated plasma, bone marrow aspirate, concentrated bone marrow aspirate or combinations thereof.

In one illustrative embodiment, the aqueous demineralized bone extract may be an acid soluble demineralized bone extract. The acid soluble extract may be produced by mixing demineralized bone matrix (DBM) with a weak acid such as, but not limited to citric acid, acetic acid, lactic acid, malic acid or mixtures thereof. The mixture may be stirred or agitated from about 8 hours to about 96 hours at a temperature not greater than 50° C. At temperatures greater than 50° C. there may be inactivation of the growth factors and/or proteins. The extract may then be filtered to remove any remaining solids, the acid neutralized or removed and used to coat the porous biocompatible structure.

In another illustrative embodiment, the aqueous demineralized bone extract may be a guanidine hydrochloride demineralized bone extract. The guanidine hydrochloride demineralized bone extract may be produced by mixing DBM with a solution of guanidine hydrochloride where the guanidine hydrochloride may be from about 3M to about 6M. The mixture may be stirred or agitated from about 8 hours to about 96 hours at a temperature not greater than 50° C. The extract may then be filtered to remove any remaining solids, the guanidine hydrochloride neutralized or removed and used to coat the porous biocompatible structure. Although not wishing to be bound by theory, the guanidine hydrochloride demineralized bone extract may have a higher protein content than the acid soluble demineralized bone extract as it may be more likely to dissolve some of the DBM.

The aqueous demineralized bone extract coating may be applied to the porous biocompatible structure in a manner that allows for the coating to be delivered to the pores and passageways. For example, the coating may be applied under vacuum.

Alternatively, the coating may be applied by placing the material in the extract and allowing the extract to enter the pores and passageways by capillary action. Once the coating is applied to the biocompatible structure it may be dried onto the structure.

In another embodiment the biomaterial of the present invention may further comprise a demineralized bone gelatin coating. The demineralized bone gelatin coating may be formed from the remaining solids after the extract is filtered or it may be formed from a different demineralized bone sample. Alternatively, it may be formed from partially purified or isolated collagen. The demineralized bone or collagen may be mixed with a saline solution, water or any other biocompatible solution and heated under pressure to dissolve the demineralized bone matrix or collagen to form the demineralized bone gelatin coating. The coating may then be coated over the demineralized bone extract coating or it may be mixed with the demineralized bone extract coating and the mixture of the extract and gelatin coatings may then be applied to the biocompatible structure to give only a single coating. The demineralized gelatin coating is applied such that it coats the pores and the passageways. As with the demineralized bone extract coating, the gelatin coating, either alone or combined with the extract coating, may be applied under vacuum or it may coat the pores through capillary action. After application to the biocompatible structure, the demineralized bone gelatin coating may be dried. The demineralized bone gelatin coating may be less viscous at higher temperatures making it easier to apply to the biocompatible structure. However, care should be taken so that the demineralized bone gelatin coating is not at a temperature high enough to inactivate the growth factors and/or proteins of the demineralized bone extract coating.

It will be appreciated that although the embodiments describe a single coating, more than one coating of either the extract and/or the gelatin may be applied. If more than one coat is applied, the individual coats may be dried before the next coat is applied.

In one embodiment, the present invention provides a method of preparing a biomaterial comprising mixing DBM with an aqueous solution of a weak acid or guanidine hydrochloride with constant agitation for a set amount of time to produce an aqueous demineralized bone extract, filtering the extract solution to remove any remaining solids, neutralizing or removing the weak acid or guanidine hydrochloride and coating the porous biocompatible structure with the extract. The amount of DBM may be from about 2 g to about 10 g per 100 g of solution. The DBM may be in any form, including, but not limited to, powder, granules, fragments, slices, pellets, slices or shavings. It will be appreciated that the concentration of growth factors and/or proteins in the extract may be related to both the amount of DBM used and the form, as well as the strength of aqueous solution. The aqueous solution may comprise any biologically compatible aqueous solution, particularly those in which growth factors and proteins may be stable in. Examples of such solutions may be, but not limited to, Tris buffer, Tris buffered saline, phosphate buffer and phosphate buffered saline. In one illustrative embodiment, the solution may be a weak acid solution where the weak acid may be, but not limited to, citric acid, lactic acid, malic acid, ascorbic acid or combinations thereof. Any weak acid known in the art may be used. The concentration of the weak acid solution may be from about 2 M to about 3 M. In a second illustrative embodiment, the solution is a guanidine hydrochloride solution where the concentration of the guanidine hydrochloride solution may be from about 3 M to about 6 M.

The DBM may be mixed with the aqueous solution for a set amount of time with constant agitation at a temperature not greater than 50° C. The amount of time that the DBM and aqueous solution may be mixed may be from about 8 hours to about 96 hours. In one illustrative embodiment, the DBM and aqueous solution may be mixed together from about 24 hours to about 96 hours. The DBM and aqueous solution may be mixed together with constant agitation during that time. Constant agitation may be obtained by, but not limited to, stirring, shaking, ultrasound or any combination thereof as well as any other methods of agitating a mixture. The mixing may be carried out at a temperature that may be conducive to extracting growth factors and/or proteins from the DBM, but where growth factors and/or proteins may be stable. In an illustrative embodiment, the temperature may be no greater than 50° C. In another illustrative embodiment, the temperature may be room temperature.

After mixing for the appropriate amount of time, the resulting demineralized bone extract may be separated from any insoluble DBM remaining. This separation may occur by any number of processes such as, but not limited to, decanting, filtering or centrifuging. In one illustrative embodiment, the solution may be filtered to remove any soluble DBM remaining. The size of the sieve or filter will depend on the size of the DBM particles remaining, which may further depend on the initial form of DBM. In one illustrative embodiment, the filter may be from about 50 microns to about 300 microns. The filter may be a sieve, paper, scintered glass, woven or non-woven fabric, or any other means of filtering that is known in the art.

The demineralized bone extract may be diluted, neutralized or the weak acid or guanidine hydrochloride removed. Methods for doing this may be, but not limited to, titration, dialysis, liquid-liquid extraction, hollow fiber filtration, ultrafiltration, crossflow filtration or precipitation. In one illustrative embodiment aqueous solution may be neutralized to a pH of from about 6.5 to about 7.5 by titration with an appropriate counterion. Such methods are well known in the art. In another illustrative embodiment, the weak acid or guanidine hydrochloride may be removed by dialysis, hollow fiber filtration, ultrafiltration or crossflow filtration against a biologically compatible buffer, such as, but not limited to, Tris, TBS, phosphate, PBS or water, where the pH of the buffer may be from about 6.5 to about 7.5. The molecular weight cutoff of the dialysis membrane will depend on the size of the proteins and/or growth factors desired in the solution. The dialysis, hollow fiber filtration, ultrafiltration or crossflow filtration membrane may have, for example, a molecular weight cut off less than or equal to 12 Kd or from about 10 Kd to about 12 Kd. It is well known in the art how to select the molecular weight cut off of dialysis tubing to retain the desired molecules within the sample.

Once neutralized, a porous biocompatible structure may be coated with the demineralized bone extract. The demineralized bone extract may be applied to the biocompatible structure such that the demineralized bone extract infiltrates the pores and passageways of the biocompatible structure. In one illustrative embodiment, the demineralized bone extract may be applied to the biocompatible structure under vacuum. In another illustrative embodiment the demineralized bone extract may be applied to the biocompatible structure by dipping the structure into the extract and allowing it to infiltrate the pores and passageways by capillary action. After the demineralized bone extract has been applied to the biocompatible structure, it may be dried onto the biocompatible structure. The demineralized bone extract may be dried onto the structure by lyophilization, vacuum, heating at a temperature not greater than 50° C. or a combination thereof.

In another embodiment, the method of the present invention may further comprise making a demineralized bone gelatin. The demineralized bone gelatin may be coated over the demineralized bone extract or it may be mixed with the extract before coating to form a single coating. The demineralized bone gelatin may be formed by mixing DBM with an aqueous saline solution such as, but not limited to PBS, TBS or a sodium chloride solution, to form a suspension. The suspension may be treated to increased temperature and pressure such as, but not limited to, autoclaved. In one illustrative embodiment, the solution may be heated to a temperature of from about 85° C. to about 130° C. at a pressure of at least about 15 psig. The DBM may be dissolved to produce a demineralized bone gelatin. Methods for forming a demineralized bone gelatin are known in the art. The DBM may be the solids removed during the filtering step while forming the demineralized bone extract or it may be fresh DBM. Alternatively, it will be appreciated that since the demineralized bone gelatin comprises mainly collagen, collagen of any purity may be substituted for the DBM.

The demineralized bone gelatin may be coated over the dried demineralized bone extract coating on the biocompatible structure such that the gelatin coats the pores and passageways. Alternatively, the demineralized bone gelatin may be mixed with the demineralized bone extract prior to the extract being coated onto the biocompatible structure to form a single coating. The single coating comprising the demineralized bone extract and gelatin may then be applied to the biocompatible structure such that the pores and passageways are coated. It will be appreciated that the demineralized bone gelatin may be less viscous at higher temperatures, making it easier to apply to the biocompatible structure. If the demineralized bone gelatin is applied to the biocompatible structure in a less viscous form such as a solution, it should be allowed to gel before any other steps are performed. Care should be taken so that the demineralized bone gelatin coating is not at a temperature high enough to inactivate the growth factors and/or proteins of the demineralized bone extract coating.

Once applied, the demineralized bone gelatin, either alone or mixed with the demineralized bone extract, may be dried onto the biocompatible structure. The demineralized bone gelatin may be dried onto the structure by lyophilization, vacuum, heating at a temperature not greater than 50° C. or a combination thereof.

It should be understood, of course, that the foregoing relates to exemplary embodiments of the invention and that modifications may be made without departing from the spirit and scope of the invention as set forth in the following claims.

What is claimed is:

1. A biomaterial comprising:
   a porous biocompatible structure comprising interconnected pores, wherein the pores comprise interior walls and are interconnected by passageways;
   an aqueous demineralized bone extract coating comprising growth factors, proteins or a combination thereof, wherein the aqueous demineralized bone extract coating is formed by dissolving soluble demineralized bone matrix in an aqueous solution comprising at least one of a weak acid or guanidine hydrochloride; and
   a demineralized bone gelatin coating comprising a demineralized bone matrix gelatin comprising demineralized bone matrix suspended in an aqueous saline solution, wherein the aqueous saline solution is heated to dissolve the demineralized bone matrix to form the demineralized bone matrix gelatin;
   wherein the demineralized bone extract coating and the demineralized bone gelatin coating cover the interior walls and passageways.

2. The biomaterial of claim 1, wherein the aqueous demineralized bone extract coating and the demineralized bone gelatin coating are combined into a single coating material which covers the interior walls and passageways.

3. The biomaterial of claim 1, wherein the aqueous demineralized bone extract coating covers the interior walls and passageways and the demineralized bone gelatin coating covers the aqueous demineralized bone extract coating.

4. The biomaterial of claim 1, wherein the aqueous demineralized bone extract coating and the demineralized bone gelatin coating are dried on the interior walls and passageways.

5. The biomaterial of claim 1, wherein the aqueous demineralized bone extract coating is an acid soluble demineralized bone coating.

6. The biomaterial of claim 1, wherein the aqueous demineralized bone extract coating is a guanidine hydrochloride demineralized bone extract.

7. The biomaterial of claim 1, wherein the porous biocompatible structure comprises a porous metal, hydroxyapatite or xenograft demineralized cancellous bone.

8. The biomaterial of claim 7, wherein the porous metal is stainless steel, titanium, a titanium alloy, tantalum or a cobalt-chromium alloy.

9. The biomaterial of claim 7, wherein the hydroxyapatite comprises tricalcium phosphate.

10. The biomaterial of claim 7, wherein the hydroxyapatite comprises a coralline hydroxyapatite.

11. The biomaterial of claim 1, wherein the pores have a size of from about 5 microns to about 1000 microns.

12. The biomaterial of claim 1, wherein the pores have an average diameter of from about 200 microns to about 500 microns.

13. The biomaterial of claim 1, wherein the biomaterial has a form of granules, blocks, cylinders or pre-formed shapes.

14. The biomaterial of claim 1, wherein the biomaterial is used as an orthopedic implant.

15. An orthopedic implant comprising:
a porous biocompatible structure comprising interconnected pores, wherein the pores comprise interior walls and are interconnected by passageways and wherein the pores have an average diameter of from about 200 microns to about 500 microns;
an aqueous demineralized bone extract coating comprising growth factors, proteins or a combination thereof, wherein the aqueous demineralized bone extract coating is formed by dissolving soluble demineralized bone matrix in an aqueous solution comprising at least one of a weak acid or guanidine hydrochloride; and
a demineralized bone gelatin coating comprising demineralized bone matrix suspended in an aqueous saline solution, wherein the aqueous saline solution is heated to dissolve the demineralized bone matrix to form the demineralized bone matrix gelatin;
wherein the demineralized bone extract coating and the demineralized bone gelatin coating covers the interior walls and passageways, wherein the bone extract coating is dried on the interior walls and passageways.

16. The orthopedic implant of claim 15, wherein the porous biocompatible structure is coral line hydroxyapatite.

17. The orthopedic implant of claim 15, wherein the demineralized bone extract is an acid soluble extract.

18. The orthopedic implant of claim 15, wherein the demineralized bone extract is a guanidine hydrochloride demineralized bone extract.

19. The biomaterial of claim 15, wherein the demineralized bone gelatin coating and the demineralized bone extract are combined into a single coating material which covers the interior walls and passageways.

20. The biomaterial of claim 15, further comprising a demineralized bone gelatin coating, wherein the demineralized bone extract coating covers the interior walls and passageways and the demineralized bone gelatin coating covers the demineralized bone extract coating.

* * * * *